United States Patent
Rider et al.

(10) Patent No.: US 6,192,329 B1
(45) Date of Patent: Feb. 20, 2001

(54) METHOD AND APPARATUS FOR ASSESSING RISKS OF INJURY

(75) Inventors: Eugene Rider, Naperville; Daniel K. Stool, Addison, both of IL (US)

(73) Assignee: Risk Analysis & Management, Oak Brook, IL (US)

(*) Notice: Under 35 U.S.C. 154(b), the term of this patent shall be extended for 0 days.

(21) Appl. No.: 09/132,755

(22) Filed: Aug. 12, 1998

(51) Int. Cl.$^7$ .............................. G06G 7/48; G06B 23/28
(52) U.S. Cl. .................... 703/6; 703/1; 128/922; 434/262; 434/267; 434/270
(58) Field of Search ............... 395/500.28, 500.01, 395/120, 121; 600/407; 434/270, 262, 267; 433/6; 705/2; 703/1, 7; 128/922

(56) References Cited

U.S. PATENT DOCUMENTS

| | | | |
|---|---|---|---|
| 4,504,225 | * | 3/1985 | Yoshii ........................... 433/6 |
| 5,452,407 | * | 9/1995 | Crook ............................ 395/121 |
| 5,454,069 | * | 9/1995 | Knapp et al. ................. 395/120 |
| 5,505,623 | * | 4/1996 | Chernack et al. ............ 434/272 |
| 5,741,215 | * | 4/1998 | D'Urso .......................... 600/407 |
| 5,846,087 | * | 12/1998 | Scherer ......................... 434/270 |
| 6,062,866 | * | 5/2000 | Prom ............................. 434/268 |
| 6,112,109 | * | 8/2000 | D'Urso .......................... 600/407 |

OTHER PUBLICATIONS

J. S. Reilly et al., "Prevention And Management Of Aerodigestive Foreign Body Injuries In Childhood", *Pediatric Otolaryngology*, vol. 43, No. 6, Dec. 1996, pp. 1403–1411.

F. L. Rimell et al., "Characteristics Of Objects That Cause Choking In Children", *Original Contributions*, vol. 274, No. 22, Dec. 13, 1995, pp. 1763–1766.

D.Stool, G. Rider & J. Welling, 'Human Factors project: Development of computer models of anatomy as an aid to risk management', received by publisher Dec. 17, 1996, Int. Jrnl of Pediatric Otorhinolaryngology vol. 43 pp. 217–227.*

* cited by examiner

Primary Examiner—Kevin J. Teska
Assistant Examiner—Lonnie A. Knox
(74) Attorney, Agent, or Firm—Finnegan, Henderson, Farabow, Garrett & Dunner, L.L.P.

(57) ABSTRACT

Children, particularly those younger than 4 years, frequently place foreign objects such as toys and small parts of consumer products in their mouths, nasal cavities and ear canals. These actions not infrequently lead to injury or death. To asses the risk of injury or death in children at the critical stages of child development, accurate computerized and physical models of anatomical areas including the oral cavity, orbit, ear canal and nasal passages that are most often severely injured by foreign body impaction are created. These computer and physical anatomical models are used in combination with computer and physical models of products to assess the possible hazards inherent in a product design and to communicate the risks associated with product design to manufacturers and marketing groups.

22 Claims, 18 Drawing Sheets

METHOD AND APPARATUS FOR ASSESSING RISKS OF INJURY

BACKGROUND OF THE INVENTION

The present invention relates generally to assessing the risk of injury to a child by a product, and more particularly to using computer and physical anatomical models of young children in conjunction with computer and physical models of a product to determine the risk of injury to a child from that product.

For young children, particularly those younger than 4 years old, placing objects of all kinds in their mouths or other body orifices is normal developmental behavior. However, this behavior carries risk of injury and, in the case of foreign bodies that become impacted in the airway, death by asphyxiation.

A study of choking in young children examined the characteristics of objects that had caused serious aerodigestive tract (airway, cricopharyngeal, or esophageal) injury, as indicated by the need for operative removal, or death due to choking as reported to the Consumer Product Safety Commission (CPSC). The results confirmed previous reports in the medical literature that the risk of injury or death posed by a food, toy or toy part, or another object depends upon its size, shape, and consistency.

The study used a computer-simulated Small Parts Test Fixture (SPTF) to analyze the characteristics of 101 rigid, three-dimensional objects that caused young children to choke to death. According to Part 1501 of the Federal Hazardous Substances Act, an object intended for use by small children will be approved for interstate commerce if it does not fit within the SPTF, a rigid cylindrical device designed to simulate the young child's airway. Of the 101 objects that had caused children's deaths, fourteen (14) passed the SPTF test. Thus, fourteen objects that did not fit completely within the SPTF had caused children's deaths. These results indicate that a more accurate means to assess risk is needed.

The assessment of risk posed by various objects for causing impaction injury or death can be improved in two ways. First, "research tools" used to assess the risk of impaction should more closely model the irregular shapes of the body cavities being studied. Second, because a child's anatomy changes with development, models should be developed of various body cavities for children of different ages.

SUMMARY OF THE INVENTION

Systems and methods consistent with the present invention use anatomically accurate, age-indexed models of children's body cavities to assess the hazards of impaction with various toys or toy parts. In particular, modern computer-aided design (CAD) techniques are used to develop several models of the oral cavities and airways, nasal passages and sinuses, and external auditory canals of young children of various ages. In addition, physical models corresponding to the computer simulated models are used to assess the hazards of impaction with toys and toy parts in oral cavities and airways, nasal passages and sinuses, and external auditory canals of young children of various ages.

A method consistent with the present invention for forming a physical model of a head for assessing injury risks includes the steps of obtaining digital images of an external head, skull, and at least one cavity of a human head, generating stereo lithographic solids for the digital images of the external head, skull and at least one cavity, creating molds of the external head, skull and at least one cavity using the corresponding stereo lithographic solids, casting moldable material into the mold of the at least one cavity, attaching together the molds of the external head, skull and at least one cavity, pouring a hardener into the mold of the external head, and removing the moldable material in the mold of the at least one cavity to create an opening in the at least one cavity after the moldable material has cured.

Both the foregoing general description and the following detailed description provide examples and explanations only. They do not restrict the claimed invention.

DESCRIPTION OF THE DRAWINGS

The accompanying drawings, which are incorporated in and constitute a part of this specification, illustrate embodiments of the invention and, together with the description, explain the advantages and principles of the invention. In the drawings.

DESCRIPTION OF THE PREFERRED EMBODIMENT

Figure 1:
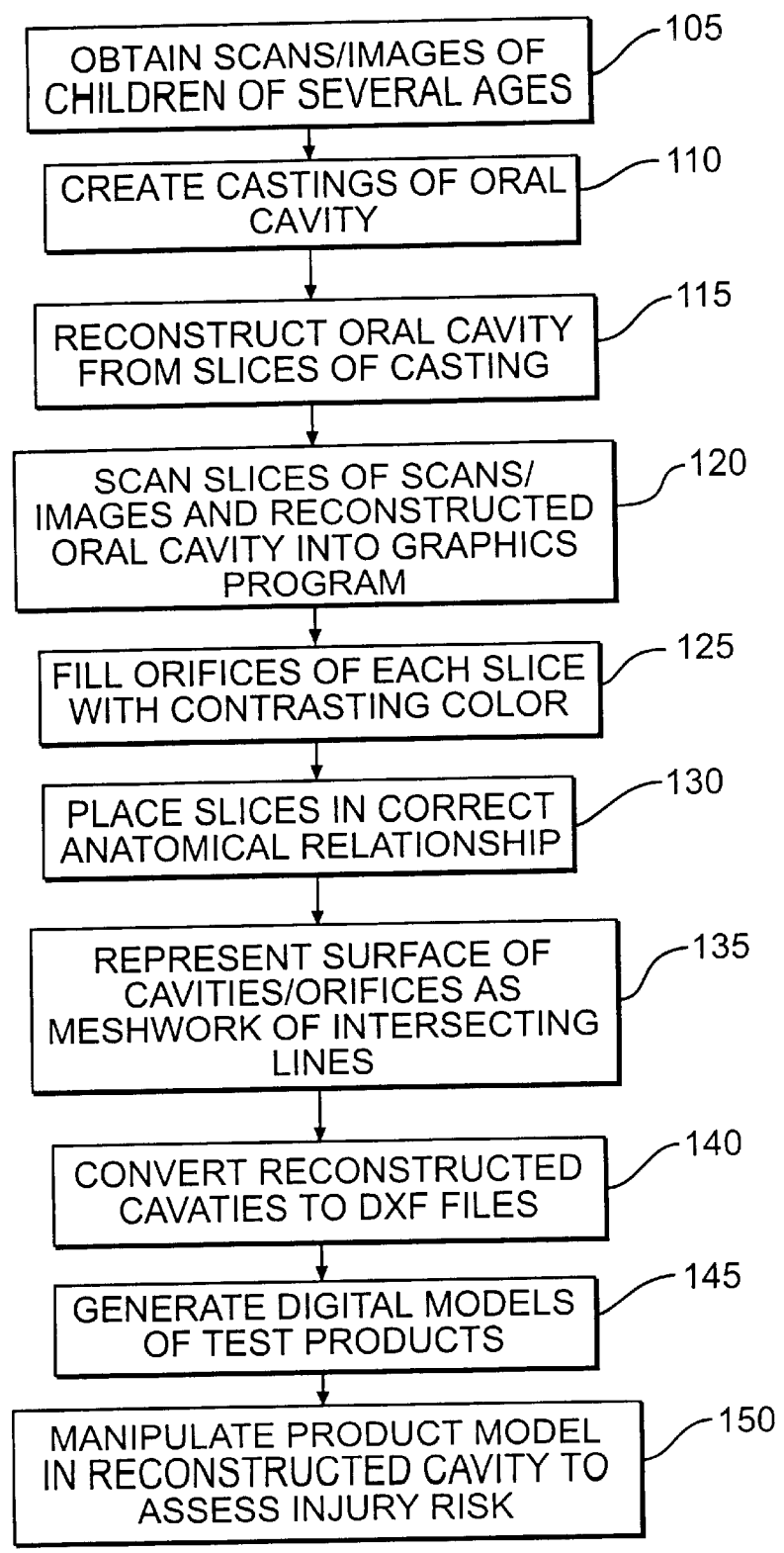
FIG. 1 is a flow chart consistent with the present invention for creating a computer model of children of various ages.

Reference will now be made to preferred embodiments of this invention, examples of which are shown in the accompanying drawings and will be obvious from the description of the invention. In the drawings, the same reference numbers represent the same or similar elements in the different drawings whenever possible.

To more accurately assess the risk of toys and products used by children, systems and methods consistent with the present invention use both a computer and physical model of children of various ages in combination with computer and physical models of the products. The computer model can provide assessments of the risks of a product as well as assist in the development of accurate physical models. The physical model can provide additional assessments of the risks of a product that may be difficult to communicate using the computer model.

The following is a description for developing the computer model consistent with the present invention. Models of the auditory canals, nasal passages, airways and oral cavities of children 1, 2, 3, and 4 years old use data obtained by tomographic imaging techniques and manipulated with common computer graphics and computer-aided design (CAD) software programs running on personal computers. The specific techniques for data acquisition and manipulation vary slightly according to the size and complexity of the cavity. CAD techniques help assess the risk that toys, toy parts, and other consumer products pose of impaction in various body cavities of children of various ages.

FIG. 1 shows a flow chart consistent with the present invention for creating a computer model of children of various ages. To construct models of the airways, auditory canals and nasal passages of young children, serial computed tomography (CT) scans or magnetic resonance (MR) images are obtained in children 1, 2, 3, and 4 years old (step 105). Each set of scans or images contains between 10 and 100 "slices" and each slice has a resolution of between 256×256 pixels and 512×512 pixels.

Because the tongue often almost completely fills the oral cavity when the mouth is closed during CT scanning or MR imaging, the shape of the oral cavity on CT scans or MR images is difficult to define. Therefore, to reconstruct the oral cavity in children 1, 2, 3, and 4 years old, castings of the mouths of patients in these age groups are made (step 110). The casts are sliced into 1.5-mm thick serial sections, and the oral cavity is reconstructed from these serial slices in the same manner as the other body cavities are reconstructed from serial CT scan or MR images slices (step 115).

The slices in each CT scan, MR image or oral cavity cast set are scanned into the computer graphics program (step 120). In each digitized slice, the orifices are filled with a continuous tone of a contrasting color (step 125). Volumetric digitized images of the auditory canals, nasal passages, and oral cavity that could be measured and manipulated digitally are obtained in a relatively straightforward manner.

After the sliced casting has been scanned into the computer graphics program and the colored area representing the cavity on each slice has been outlined, the outlined slices are placed in the correct anatomic relationship with each other (step 130). Then, the surface of the cavity is represented as a meshwork of intersecting lines that define the size (volume) of the cavity (step 135).

Figure 2:
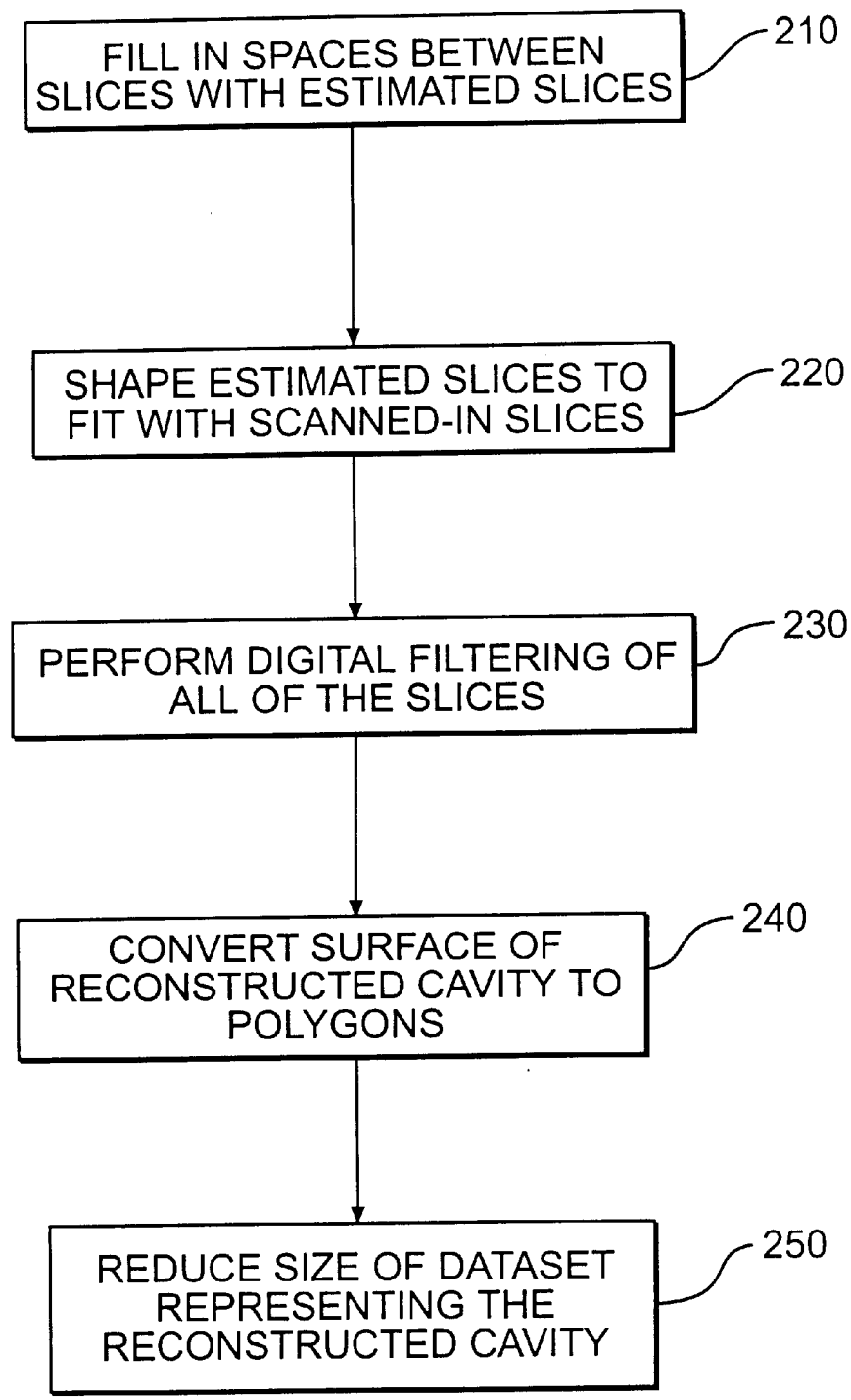
FIG. 2 is a flow chart for digitally reconstructing cavities in the computer model of FIG. 1.
Figure 3:
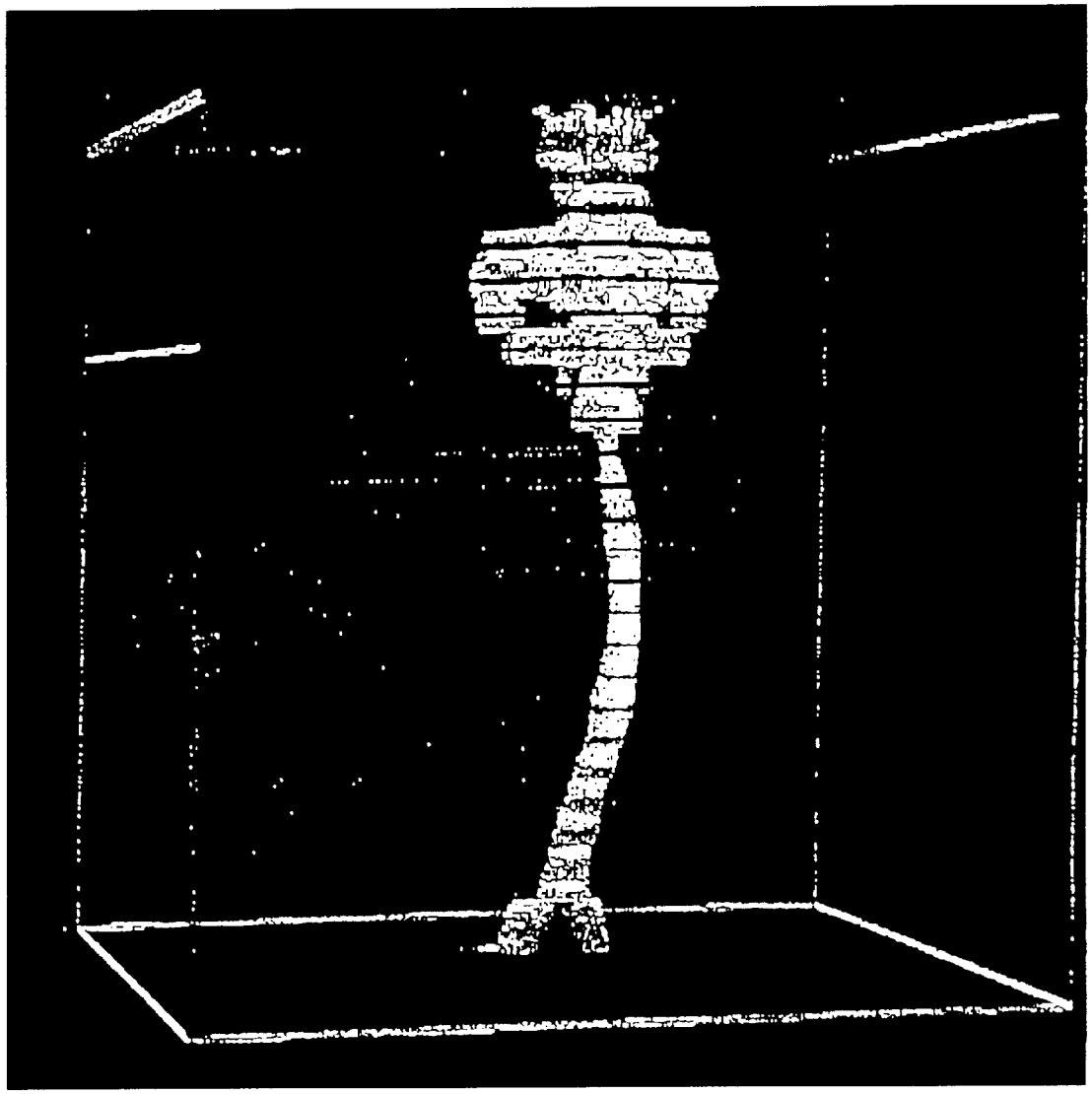
FIG. 3 is a diagram of the computer model after the filtering step of FIG. 2.

The size and complexity of the airway and sinuses necessitates the modification of the digital reconstruction process to keep the dataset representing the cavity to a manageable size. Although necessary for large cavities, such as the airway, the modification generally is applied to all cavities. FIG. 2 shows a flow chart for the modification of the digital reconstructed cavities consistent with the present invention. First, each space between scanned-in slices is "filled in" with five estimated slices (step 210). Then, a mathematical morphology process, such as the use of repeated dilation and erosion, is used to shape the intermediate slices to better fit with the scanned-in slices (step 220). For example, the data can be alternately eroded on seven or fewer neighbors and dilated on sixteen or more neighbors. The result is a reconstructed cavity with approximately 100 vertical slices and a horizontal resolution (of the slices) of either 256×256 or 512×512 pixels. Performing digital filtering of the data representing the slices one or more times decreases the horizontal resolution to 128×128 pixels as shown in FIG. 3 (step 230). Digital filtering is well known to those skilled in the art and is described, for example, by H. Hoppe et al. in "Mesh optimization," Association for Computing Machinery Computer Graphics Proceedings, Annual Conference Series, Aug. 1–6, 1993, p. 19–25, Anaheim, Calif.

Figure 4:
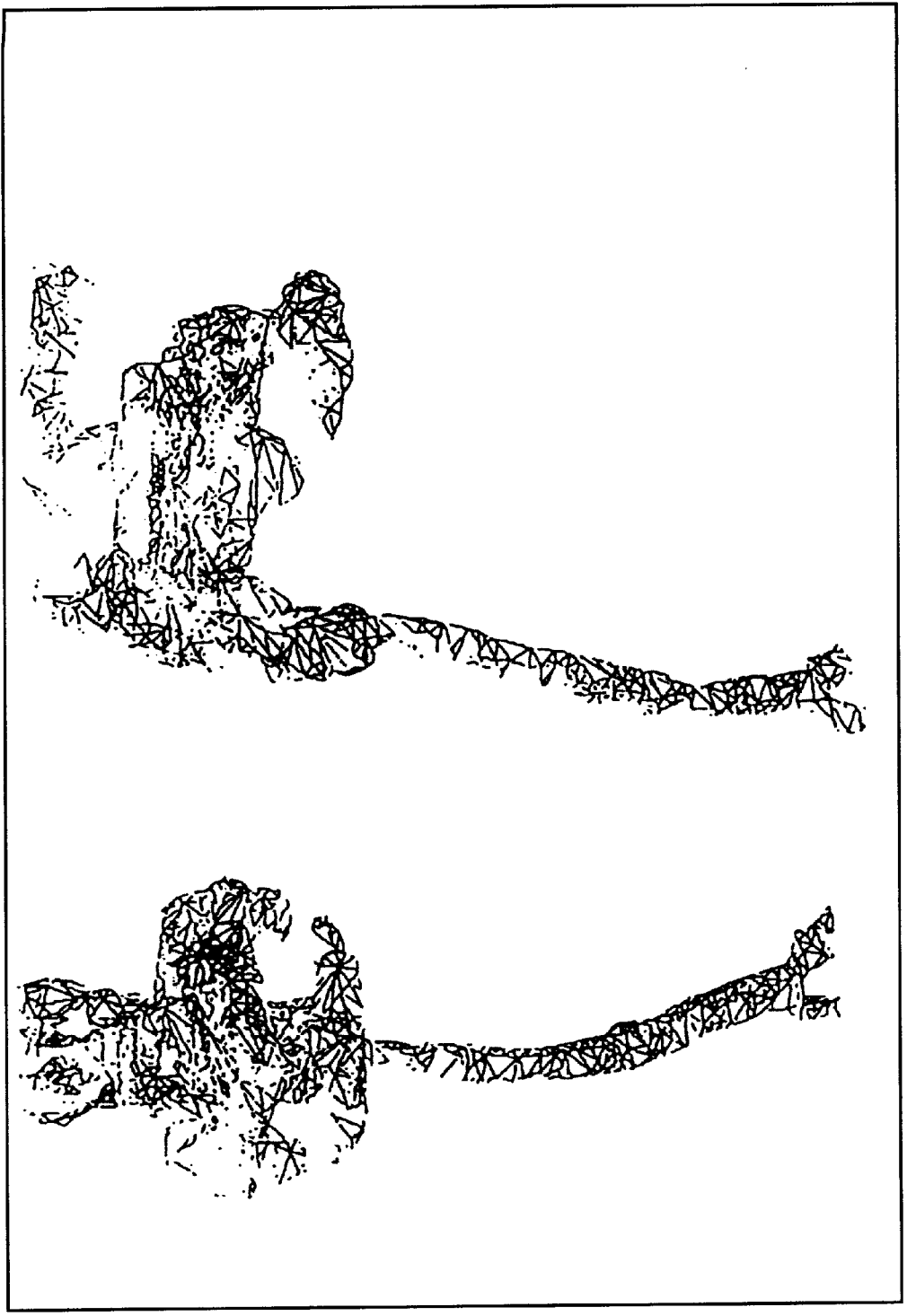
FIG. 4 is a diagram of the computer model after the conversion step of FIG. 2.

Next, the surface of the reconstructed cavity is converted to polygons using, for example, an isosurface algorithm, such as a variant of the "marching cubes" algorithm (step 240). The "marching cubes" algorithm is well known to those skilled in the art and is described, for example, by W. E. Lorenson and H. E. Klein in "Marching Cubes," Computer Graphics, Vol. 21, p. 163–69, 1987. Application of this algorithm results in the surface of the cavity being represented as a collection of triangles in three dimensions as shown in FIG. 4.

Figure 5:
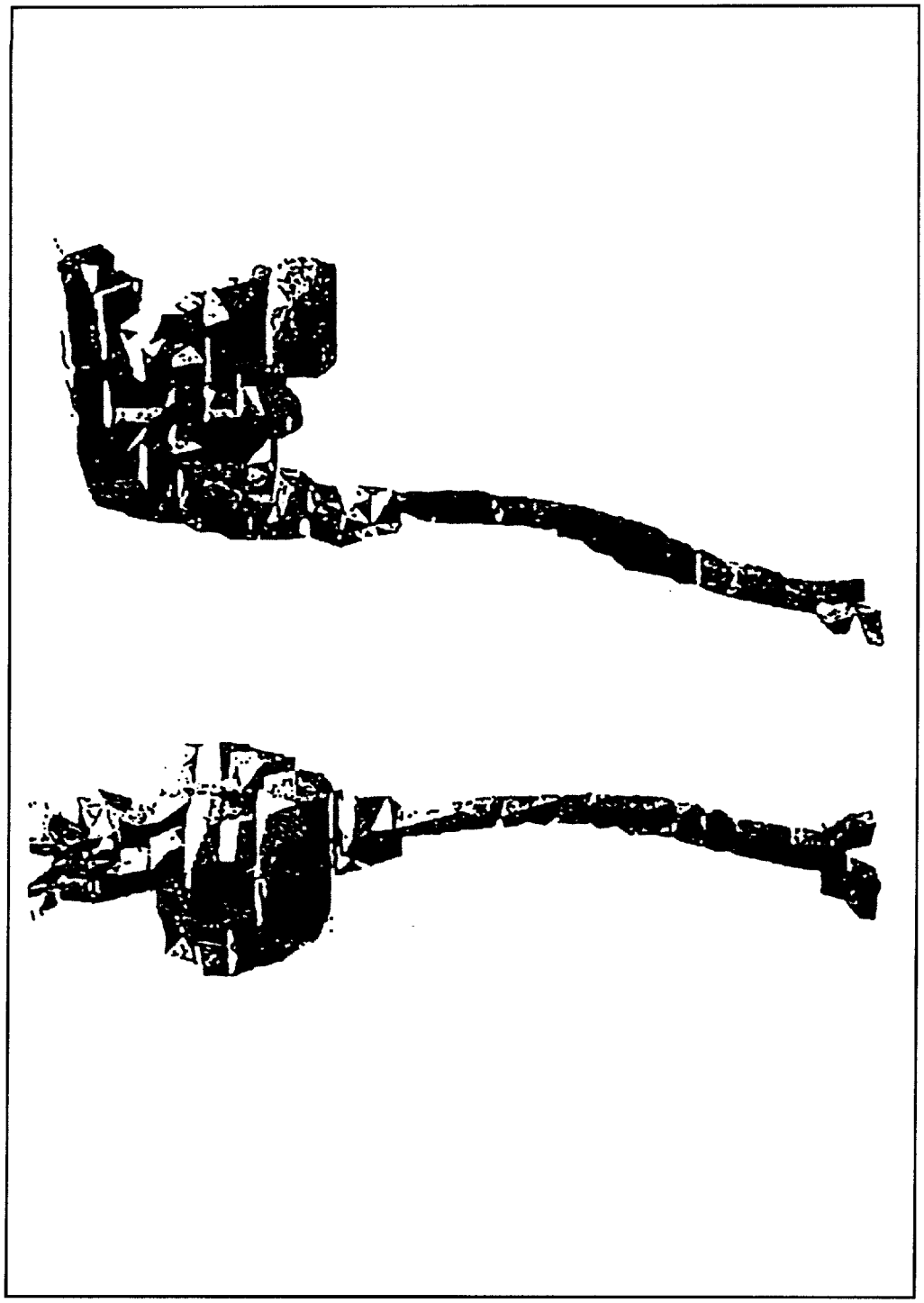
FIG. 5 is a diagram of the computer model after the reduction step of FIG. 2.

The dataset representing the isosurface of the reconstructed cavity, however, is too large for manipulation with a CAD program. In FIG. 4, for example, the reconstruction shown contains 33,500 triangles. Consequently, the last step in constructing a model of a body cavity, such as the airway, is to reduce the size of the dataset by applying, for example, a mesh optimization algorithm (step 250). Using available algorithms described, for example, by H. Hoppe et al. in "Mesh optimization," Association for Computing Machinery Computer Graphics Proceedings, Annual Conference Series, Aug. 1–6, 1993, p. 19–25, Anaheim, Calif., results in a reconstruction of the cavity that retains enough surface smoothness to be anatomically accurate while being mathematically simple enough for CAD modeling to assess the risks of foreign body impaction in the cavity as shown in FIG. 5. The example shown in FIG. 5 has 1700 triangles.

Figure 6:
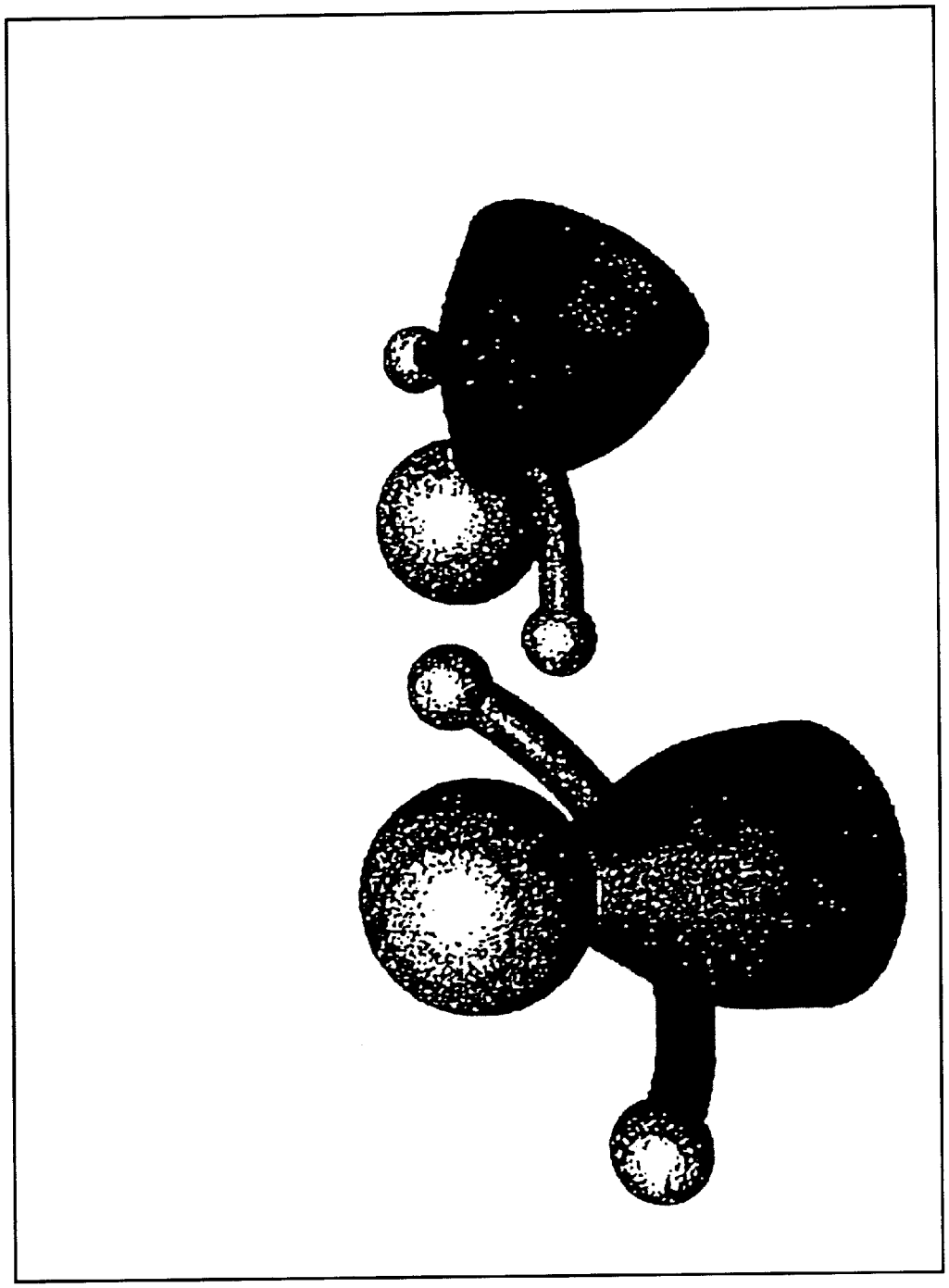
FIG. 6 is a diagram of a digital model of a product for use in conjunction with a computer model consistent with the present invention.

Returning to FIG. 1, the datasets of both small and large reconstructed body cavities are converted to digital exchange format (DXF) files for easy manipulation with a desktop CAD program (step 140). Digital models of toys, toy parts, or other consumer products are created as needed to assess risk using the CAD program (step 145). Some of these objects are initially designed using CAD, so an electronic file in the appropriate format is already available, such as shown in FIG. 6. In other cases, the size and shape of the object are digitized from existing products, prototypes or manufacturers' drawings. For example, digital models of products can be created from an injury and fatality database, which includes characteristic information of a product, such as size and shape. The database also includes for each product information about ages of affected children, their sex and the location and types of injuries caused. This latter information is particularly useful for suggesting what risks to assess for the modeled product.

To assess the risk of an object becoming impacted in a body orifice of a 1, 2, 3, or 4 year-old child, the model of the object is manipulated with the model of the appropriate orifice in the appropriate-aged child in the CAD environment (step 150, FIG. 1). This assessment can be documented by color printouts. Several sample assessments of a risk of foreign body impaction and the documented results of the performed assessments are shown in FIGS. 7–13.

Figure 7:
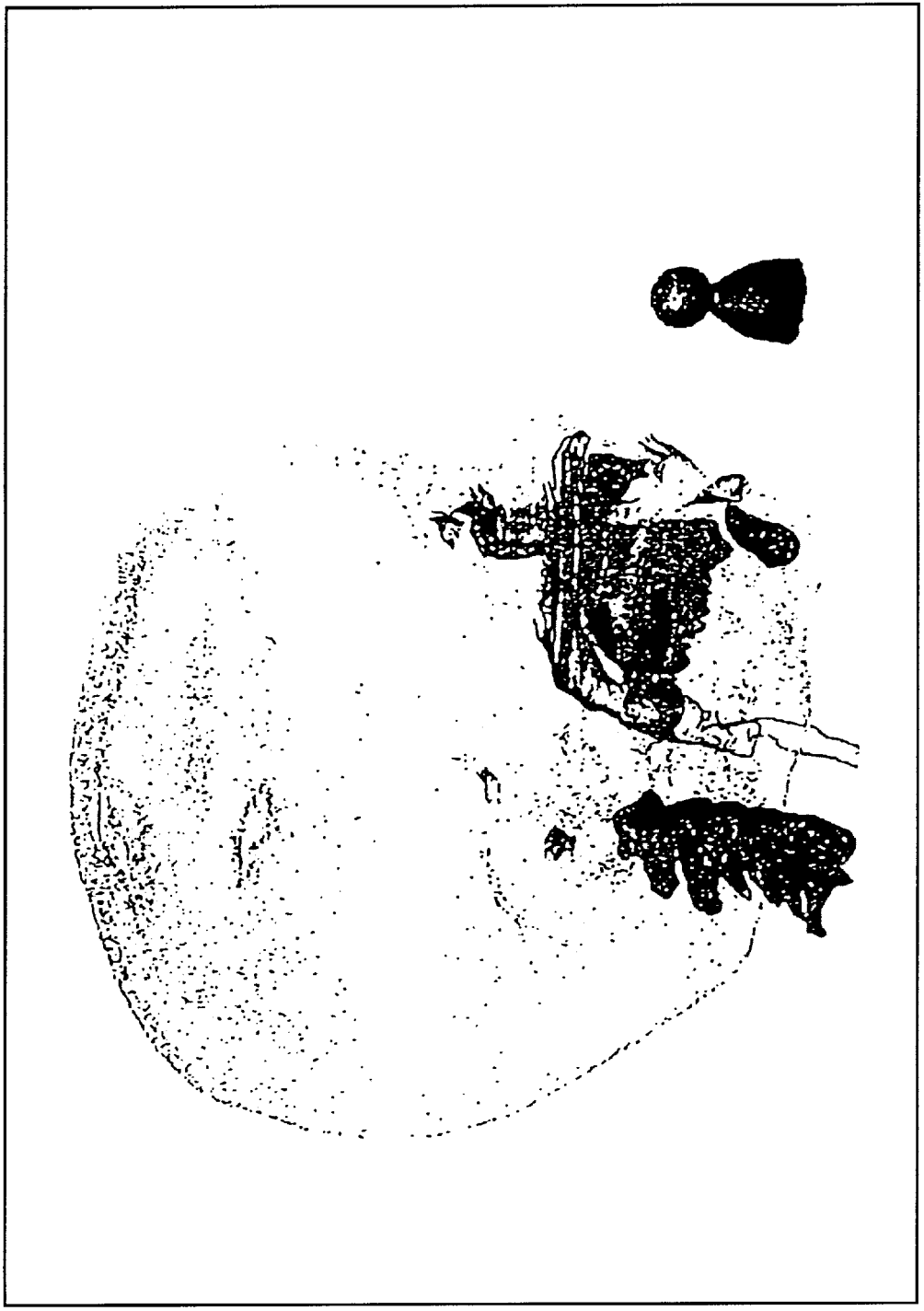
FIG. 7 is a diagram assessing the risk of a product in the oral cavity of a computer model consistent with the present invention.

Children younger than 4 years of age are particularly drawn to placing in their mouths toy characters or figurines that have been decorated with faces. Consequently, objects of this type are well represented in the fatality database. FIG. 7 shows how such objects may become impacted posterior to the palatopharyngeal arch, obstructing the airway directly and leading to asphyxiation. Although this toy meets all legal and industry standards for toy safety, including compliance with the Small Part Test Fixture criteria, it poses a substantial risk of injury. The head of this toy character is a sphere 1.0 inch in diameter, the body is conical with a diameter at the base of 1.25 inches, and the toy has an overall length of 2.0 inches. FIG. 7 shows how the spherical head of this toy can obstruct a one-year-old child's airway by fitting completely in the oropharynx and hypopharynx. The fact that the body of this toy is completely contained within the oropharynx makes the toy difficult to dislodge.

Figure 8:
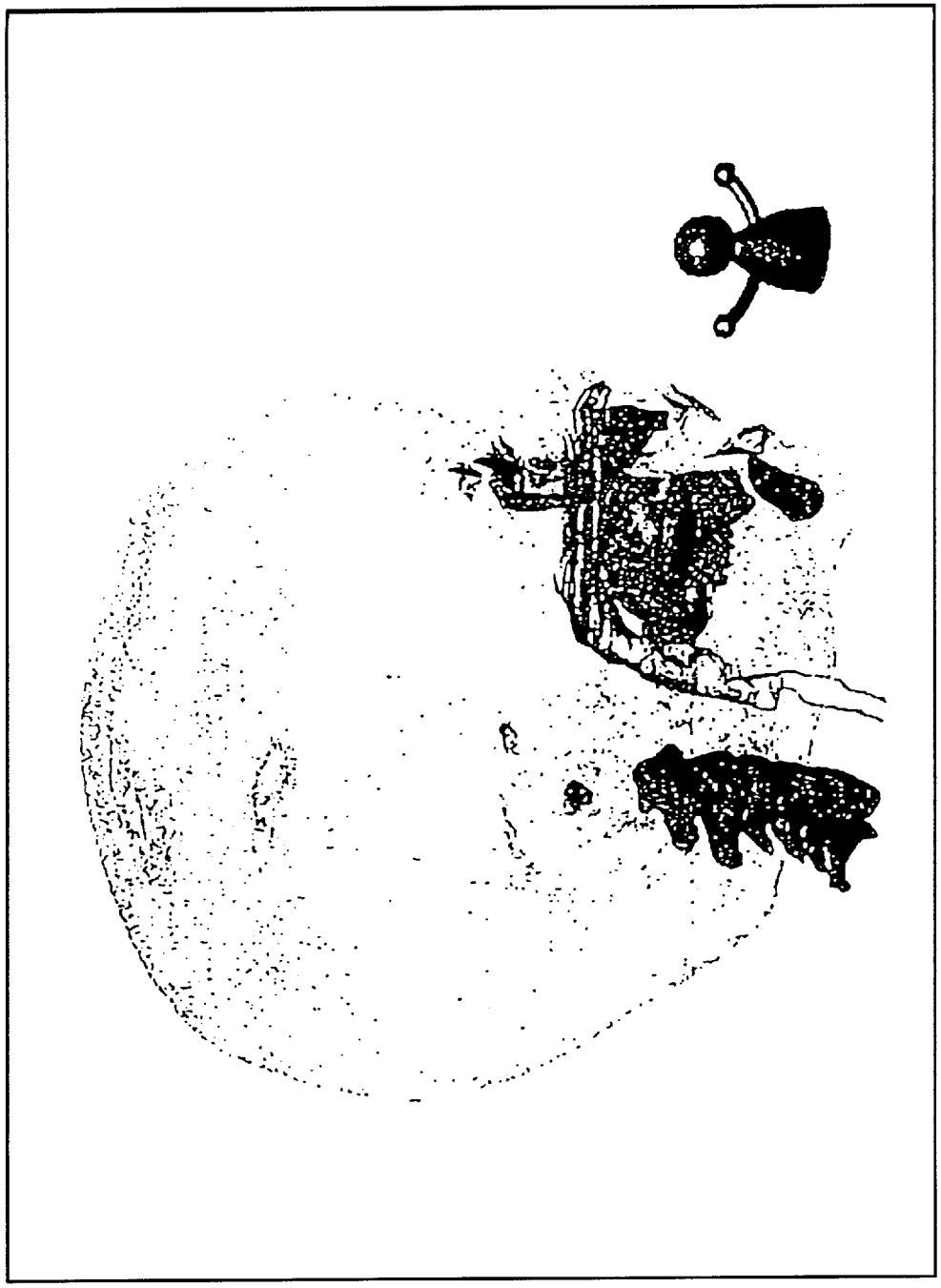
FIG. 8 is a diagram assessing the risk of a modified product in the oral cavity of a computer model consistent with the present invention.

As shown in FIG. 8, changes in the design of such toys, such as the addition of protuberances (arms, legs), can reduce the risk they pose of choking by preventing the object from reaching the back of the oral cavity.

Figure 9:
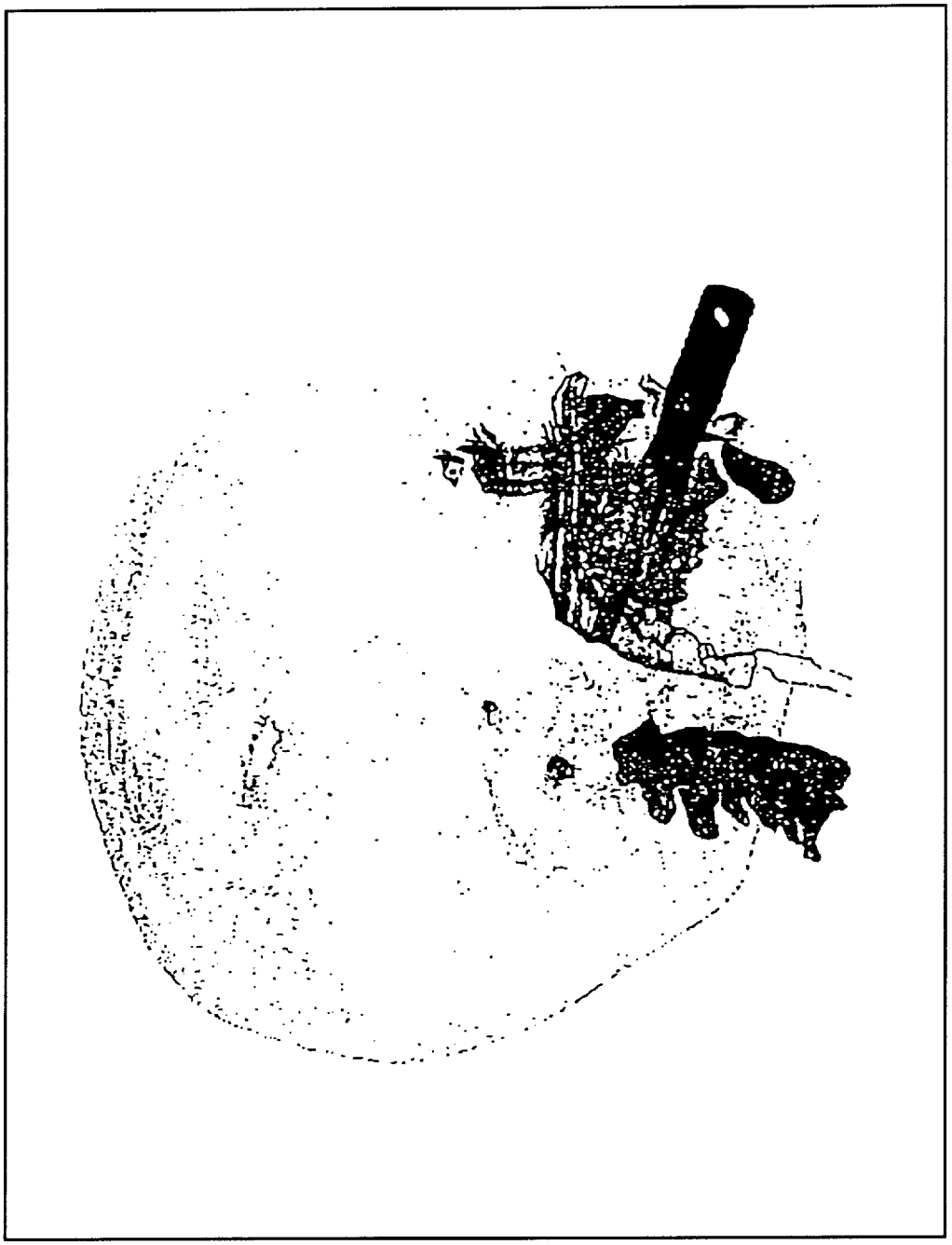
FIG. 9 is a diagram assessing the risk of another product in the oral cavity of a computer model consistent with the present invention.

FIG. 9 shows how some objects might become impacted in the oral cavity but, because the airway is not occluded, asphyxiation may be avoided. Nevertheless, children often carry objects in their mouths, and should the child fall in this situation, the object could lacerate the oral cavity or be pushed into the airway. Similarly, round but flat objects such as coins may cause injury to the oral cavity or, if swallowed, to the esophagus. However, they pose a much lower risk of asphyxiation than round three-dimensional (spherical) objects.

Figure 10:
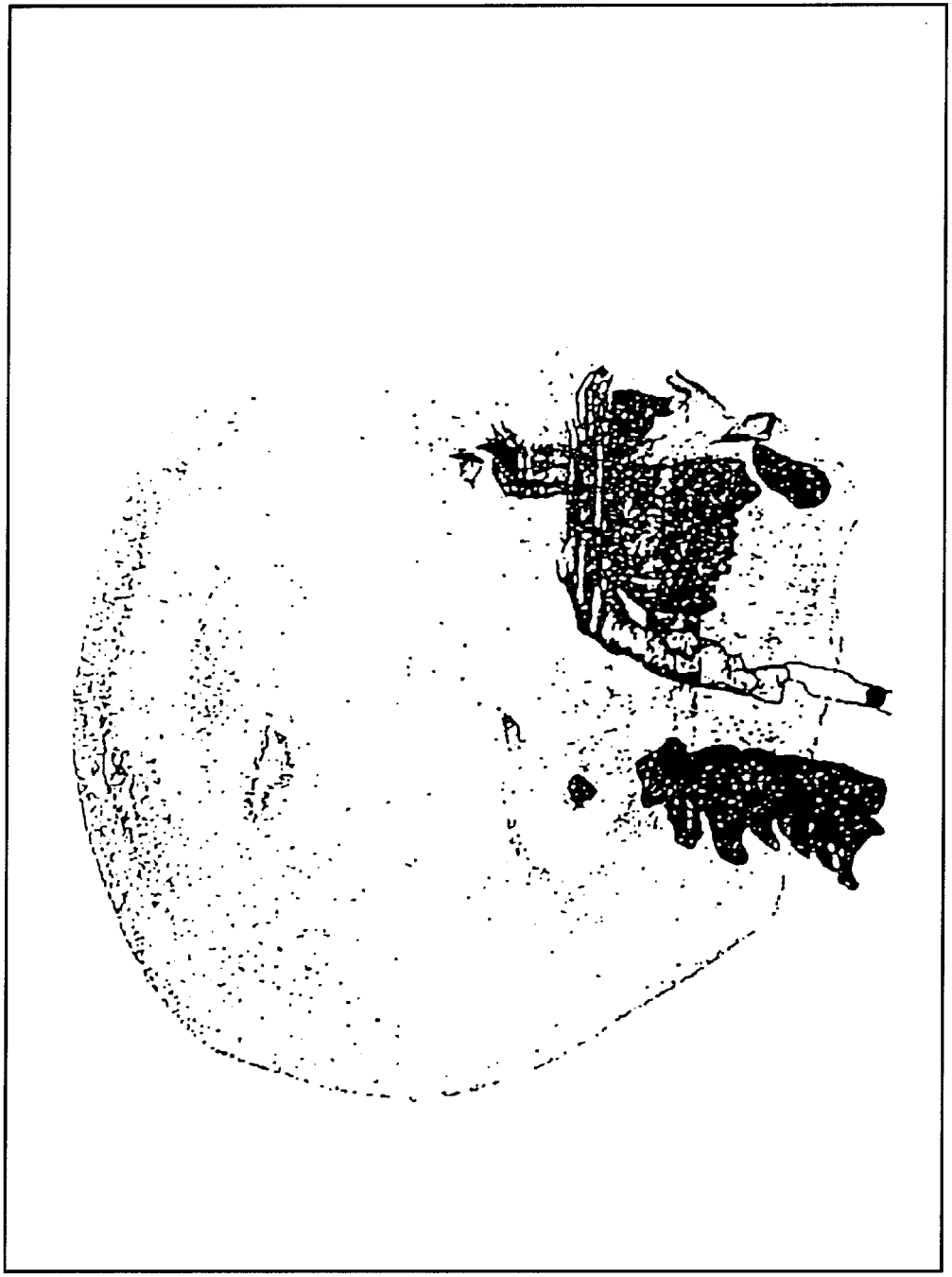
FIG. 10 is a diagram assessing the risk of a product being aspirated in a computer model consistent with the present invention.
Figure 11:
FIG. 11 is a diagram assessing the risk of a product in the auditory canal of a computer model consistent with the present invention.

FIG. 10 shows how small parts can be aspirated into the airway, causing injury or death by choking. Death by aspiration is particularly likely when the object has a part or overall form that is spheroid or ellipsoid as shown in FIG. 10. Plastic foreign bodies such as these are difficult to diagnose because they are radiolucent and thus do not appear on radiographs, CT scans, or MR images. Occasionally such foreign bodies can be located indirectly by noting displacement of tissues on radiographs or CT scans, but usually their presence must be inferred from the patient's history and symptoms.

Small parts that become impacted in the external auditory canal can lacerate the canal walls and injure the tympanic membrane. Objects that are long, thin, and rigid, such as the tail of the plastic mouse shown in FIG. 11, may even be driven though the eardrum and into the middle ear, possibly causing temporary or even permanent hearing loss in that ear. Toys, such as the plastic mouse, that pose this hazard can be redesigned to reduce this risk substantially, without affecting the play value of the product or increasing manufacturing costs.

Figure 12:
FIG. 12 is a diagram assessing the risk of a product in the nasal passage of a computer model consistent with the present invention.
Figure 13:
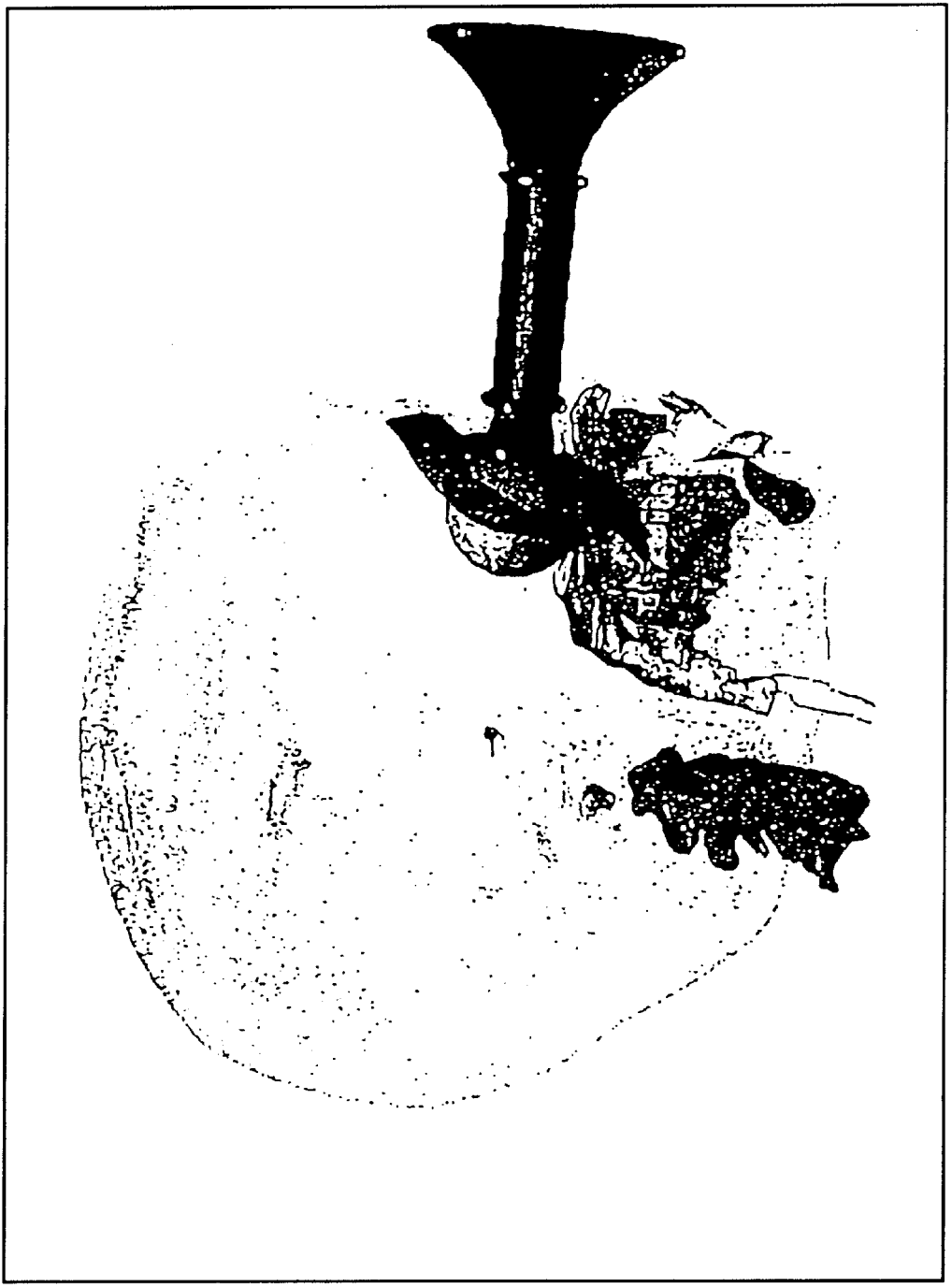
FIG. 13 is a diagram assessing the risk of a product in the eye socket of a computer model consistent with the present invention.

For most childhood foreign body injuries, the risk ratio is 60% boys to 40% girls, but this ratio is reversed for nasal impaction. This type of impaction is often first suspected when a parent notices an unpleasant odor emanating from the child's nose. FIG. 12 shows the model of a 1-year-old child with simulated nasal impaction of a small plastic peg used in a toy intended for older children. Foreign bodies in the nose must be removed carefully, to avoid aspiration or ingestion of the foreign body. Button batteries, such as are used in wristwatches, cameras, and hearing aids, are particular hazardous because corrosion of the battery shell can allow chemicals in the battery to burn tissues, possibly penetrating the nasal septum. FIG. 13 shows a model for a risk of injury from objects that are usually used close to the eye.

Figure 14:
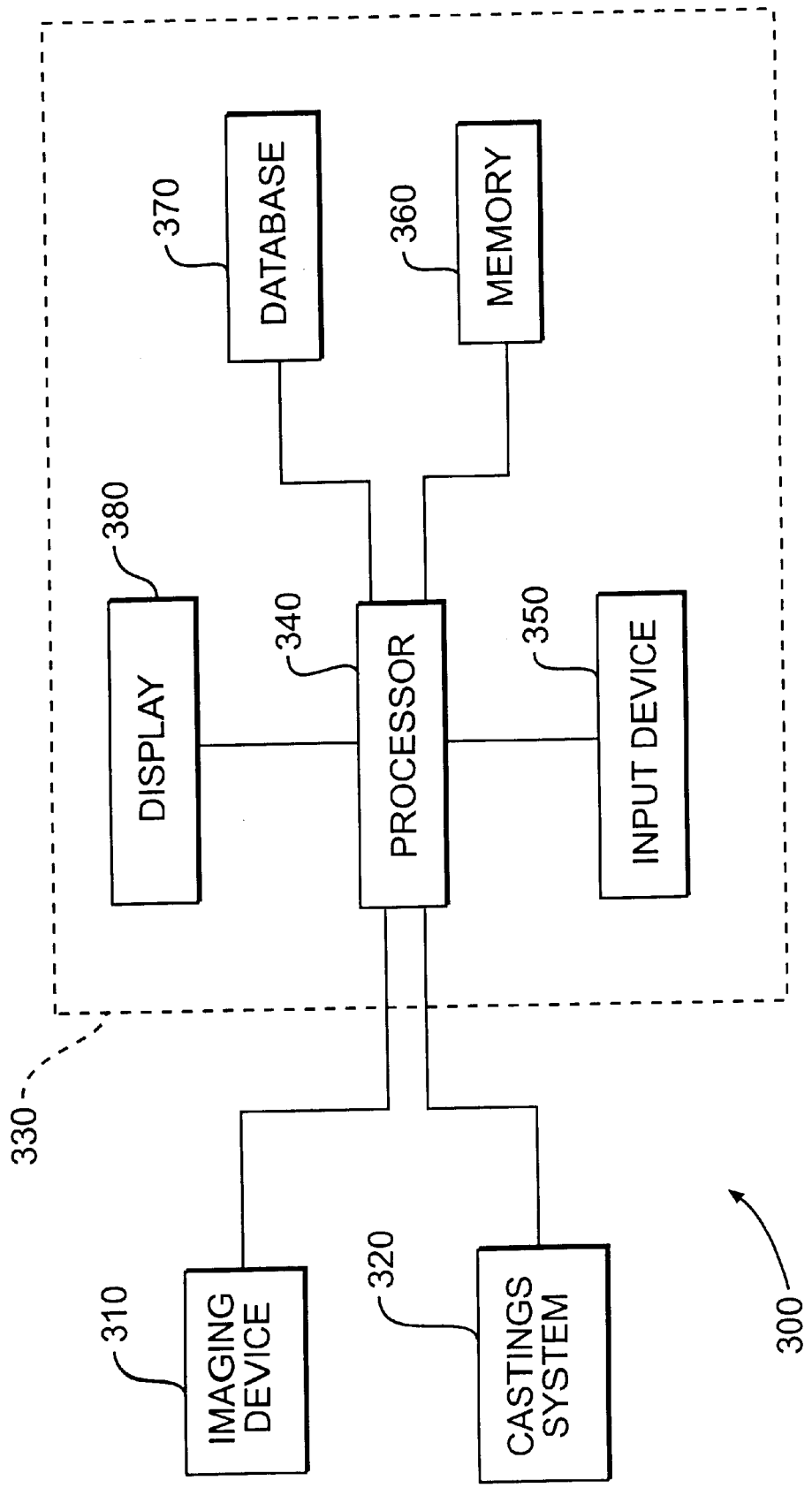
FIG. 14 is a block diagram of a computer modeling system consistent with the present invention.

FIG. 14 shows a block diagram of a computer modeling system 300 for implementing the computer modeling and analysis consistent with the present invention. System 300 includes an imaging device 310, such as a CT scan or MR imaging system, for creating digital images for the computer model and a castings system 320 for creating digital images from castings of body cavities ineffectively represented by an image generated by imaging device 310. Imaging device 310 and castings system 320 both send their images to a computer system 330.

Computer system 330 includes a processor 340, an input device 350, such as a keyboard, a memory 360, a database 370 included either in memory 360 or another memory (not shown), and a display 380. Processor 340, which may be, for example, a Pentium II processor, receives the digital images from imaging device 310 and castings system 320 and stores them in memory 360. Through input device 350, a user operates graphics programs and other processing algorithms resident in memory 360 to manipulate the stored received images into the computer model. A user can also use information from database 370 to model objects and products to test with the computer model. With these object models, a user operates a program, such as a CAD program, to assess by simulation the risk the object models pose to the computer model, as can be seen on display 380.

The anatomically accurate computer models of body cavities in children of various ages are used to simulate foreign body impaction or aspiration with a variety of toys, toy parts, consumer products, and household items. The computer models have several advantages relative to the Small Parts Test Fixture for assessment of foreign body choking or aspiration risk in small children. First, the computer-generated models provide more anatomically accurate data because they are developed using actual patient data. Further, separate digital models may be constructed for various body cavities that may be affected by impaction or aspiration of foreign bodies. Separate models for children 1, 2, 3, or 4 years old also allow risk to be assessed more specifically for various ages of children. The fact that the models and the process of risk assessment are computer-based means that risk assessments and results can be accomplished earlier in the manufacturing process, thus increasing the likelihood that changes making the product safer will be made. Lastly, the computer databases for the models and foreign objects can be modified and expanded relatively easily.

Although the computer models provide three-dimensional representations, some concepts of anatomical characteristics may be difficult to communicate to individuals with the responsibility of making risk decisions for a product. Furthermore, the computer model may not include material parameters and physical responses. As a result, the computer model may not act in the same way as a child, who has the protective mechanisms of an airway such as the gag reflex and productive cough. The material for the computer model is virtual and, as such, may not specifically have the ability to simulate the differential flexibility and material properties of actual anatomy. By using an accurate physical model, however, these limitations of the computer model can be overcome, allowing the actual demonstration of issues relevant to the anatomy with no possibility of error or ambiguity.

The physical model of a child's head includes external features such as the ear canals and oral cavity and internal anatomy such as the skull and mandible. Hollow spaces are provide in the head to depict the airway and oral cavity of the child.

Figure 15:
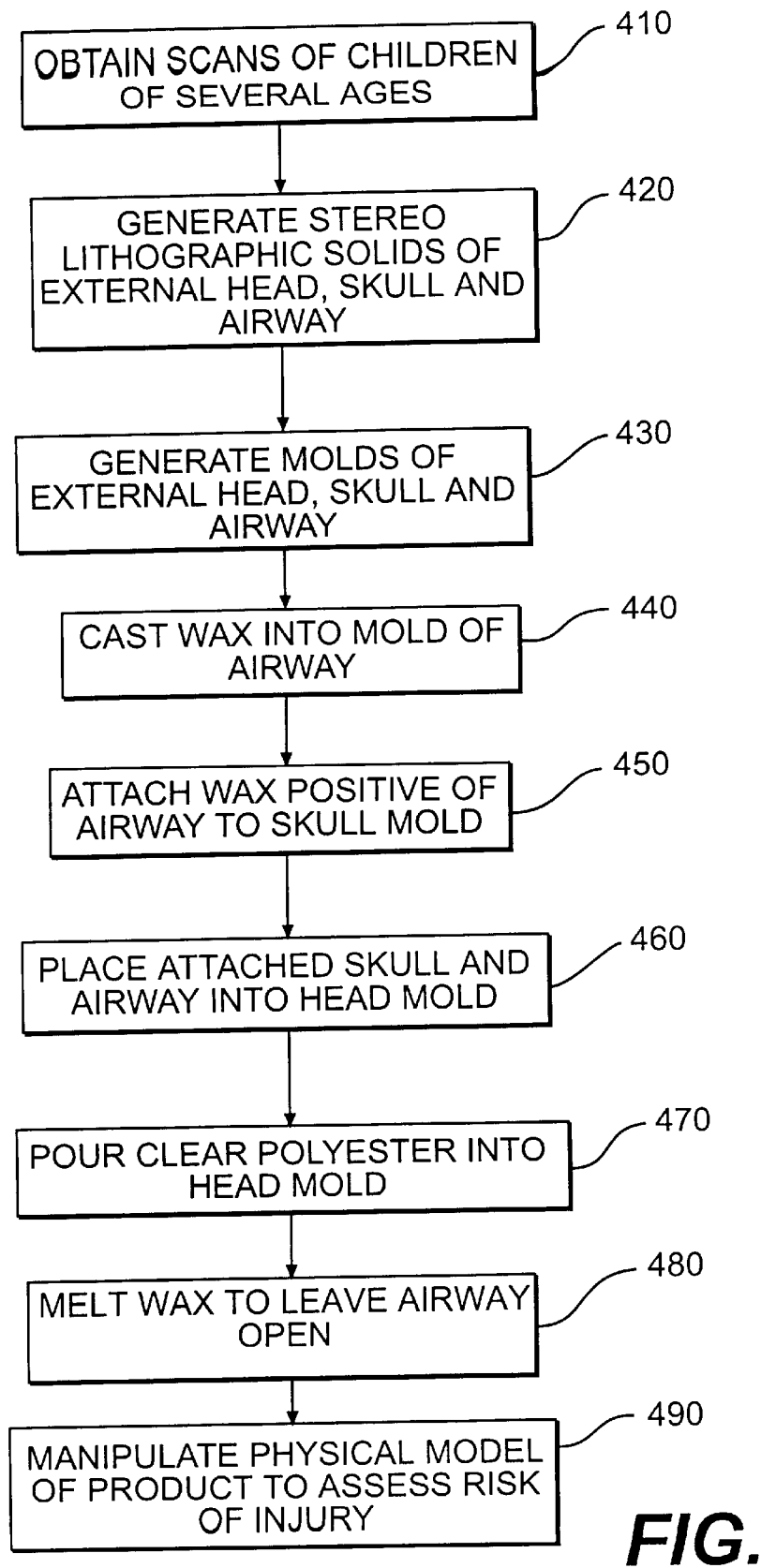
FIG. 15 is a flow chart for assembling a physical model of a child's head consistent with the present invention.
Figure 16A:
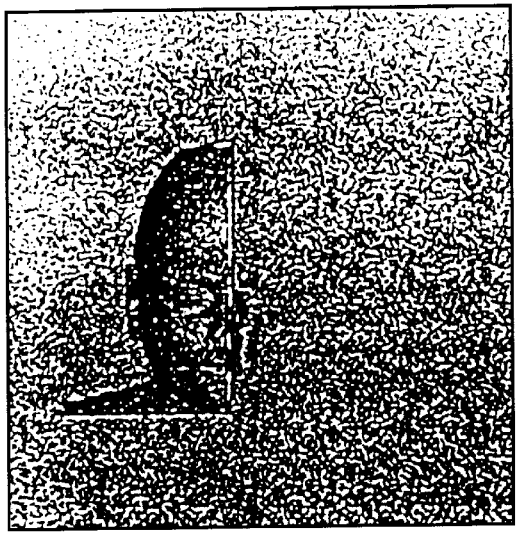
FIGS. 16A–16D are images of various views of partially constructed physical models consistent with the present invention.
Figure 16B:
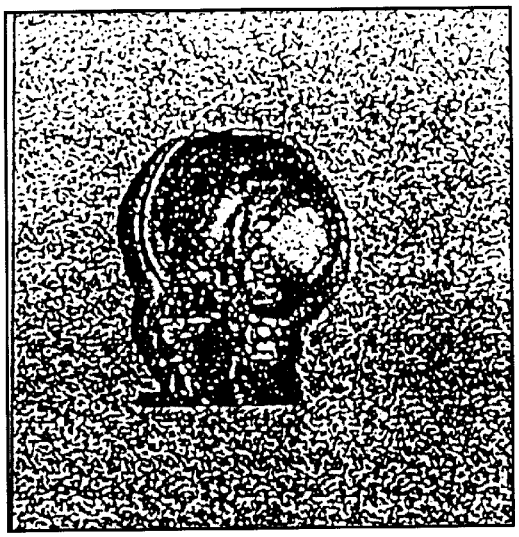
Figure 16C:
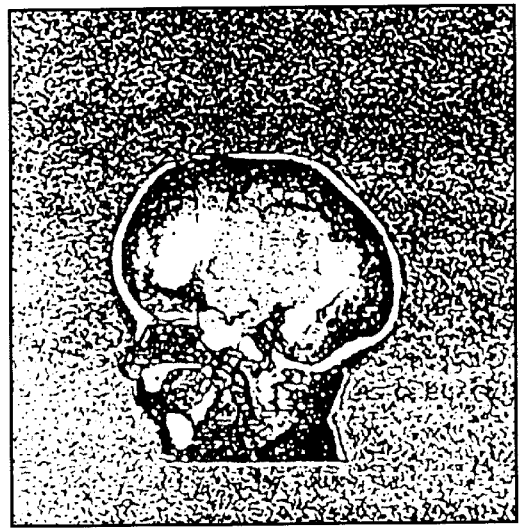
Figure 16D:

FIG. 15 shows a flow chart for creating a physical model of a child's head consistent with the present invention. First, the anatomy for the heads is acquired by obtaining data from CT scans or MR images (step 410). The scans or images are selected for their typical anatomy in the areas of interest, including the airway, skull and external head. The data from these scans or images is used to construct stereo lithographic solids of the external head, the skull and a positive of the negative space of the airway (step 420).

Molds, such as RTV silicon molds, are then made from the stereo lithographic solids of the external head, skull and airway (step 430). A wax or other moldable material with similar qualities as wax is cast only into the mold of the airway (step 440). This wax positive of the negative space is then attached to the skull mold (step 450). The subassembly of the skull and airway is placed into the head mold (step 460). After placing the subassembly into the head mold, a hardener or moldable material, such as a clear polyester, is poured into the head mold and allowed to cure (step 470). Once the polyester is cured, the wax positive of the negative space depicting the airway is removed by melting, leaving the airway open (step 480). Finally, a physical model of a test product is manipulated in the cavity of the resulting physical model of the head to assess the risk of injury to the cavity (step 490). FIGS. 16A–16D show varying views of the physical model, which includes the head or skin, the bone and the airway or windpipe. As shown in these figures, the oral cavity is solid.

Figure 17:
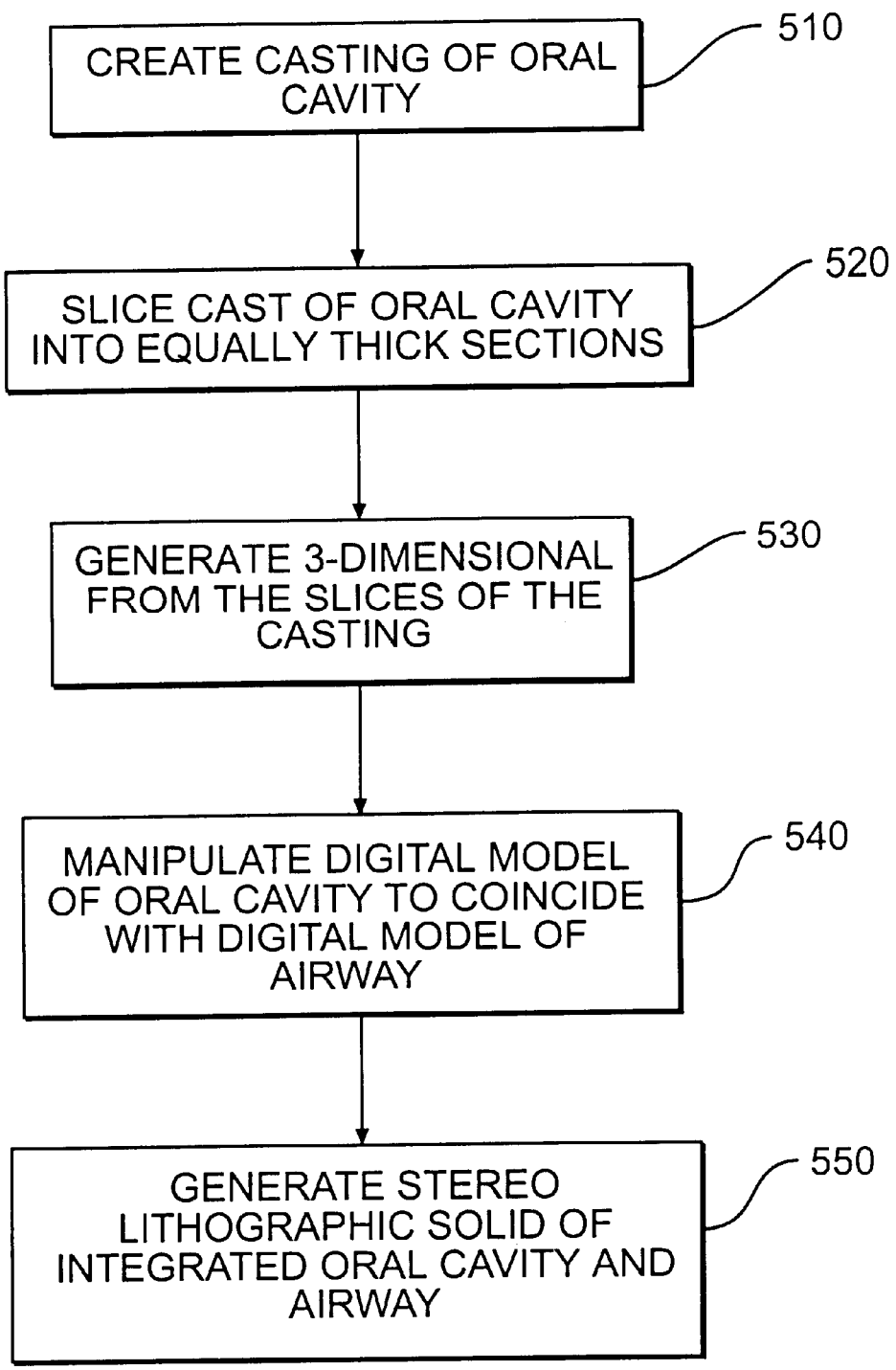
FIG. 17 is a flow chart for assembling a physical model of a child's head consistent with the present invention, which integrates the oral cavity with the airway.

It is possible, however, to also model the oral cavity and airway as a single continuous opening or cavity. FIG. 17 shows a flow chart consistent with the present invention for integrating the oral cavity with the airway in the physical model. Since a CT scan may not effectively portray the oral cavity, it may be necessary to make castings of the oral cavity (step 510). Like the computer model, the casts of the oral cavity are sliced into 1.5-mm thick serial sections (step 520), and the oral cavity is reconstructed from these serial slices to create a three-dimensional digital model in the same manner as the other body cavities are reconstructed from serial CT scan or MR image slices (step 530). Prior to the stereo lithographic step described above, the digital model of the oral cavity is manipulated with the digital model of the airway to form a digital model of a single integrated cavity (step 540). Then, a stereo lithographic solid of the integrated airway and oral cavity is constructed (step 550). After the stereo lithographic solid is constructed, the process shown in FIG. 15 is continued from step 330, which results in a physical model where the oral cavity and airway form a continuous opening.

Figure 18:
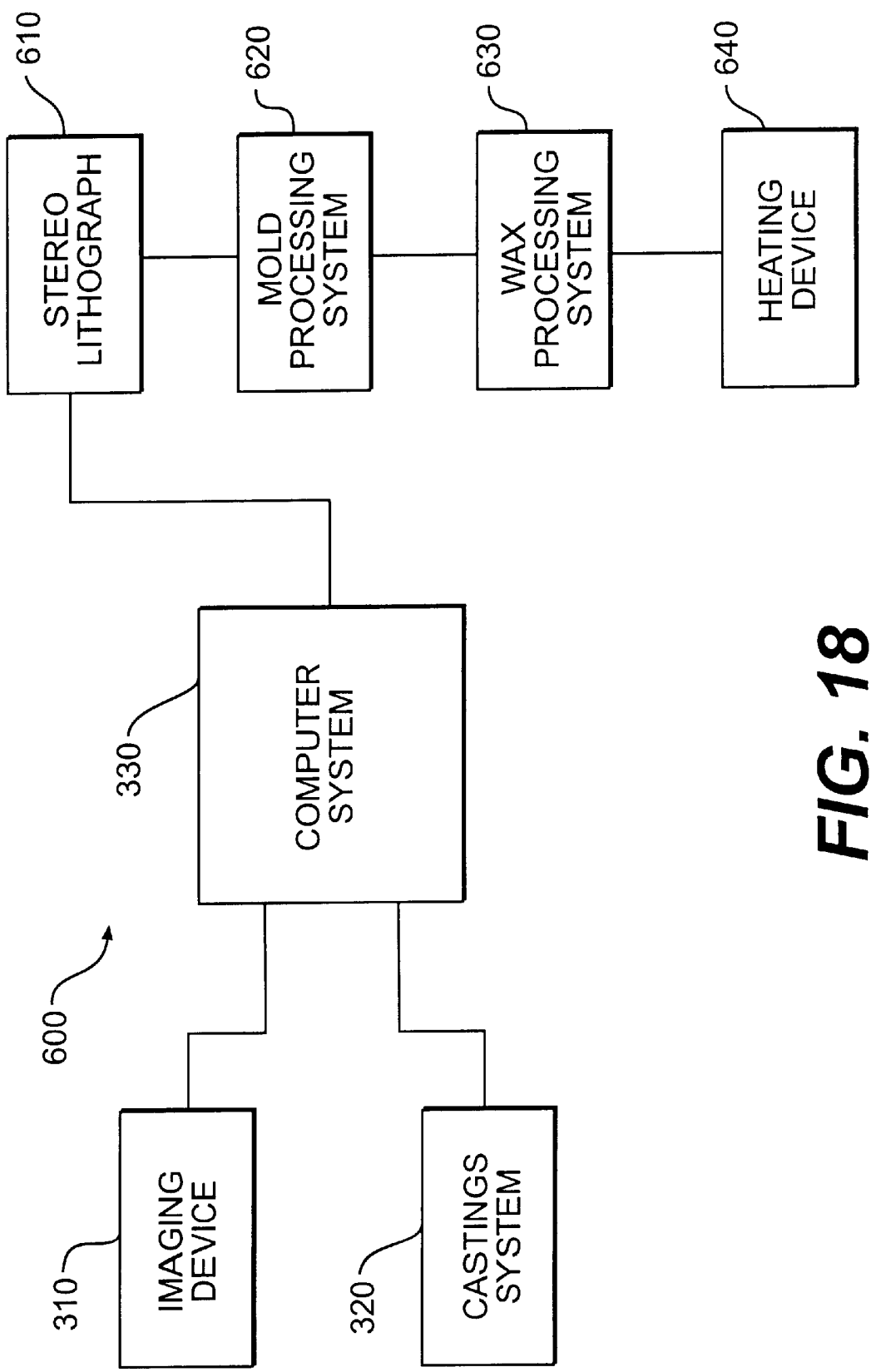
FIG. 18 shows a block diagram of a physical modeling system consistent with the present invention.

FIG. 18 shows a block diagram of a physical modeling system 600 for implementing the physical model consistent with the present invention. Like computer modeling system 300, physical modeling system 600 includes an imaging device 310, a castings system 320 and a computer system 330. Computer system is coupled to a stereo lithograph 610 and instructs it to form stereo lithographic solids according to the digital images of the external head, skull, airway and oral cavity stored in memory 360 (not shown). Stereo lithograph 610 is of conventional design and may be for example, the SLA-250 commercially available from 3D Systems.

Using the stereo lithographic solids, a mold processing system 620 creates molds for each solid. Mold processing system 620 uses a conventional design process for creating the molds from the stereo lithographic solids. The mold for the airway or combined airway and oral cavity is then processed by a wax processing system 630. Wax processing system 630 casts a wax or other suitable material in the mold of the airway or combined airway and oral cavity. Wax processing system 630 uses a conventional design process for casting wax into the mold of the airway or combined airway and oral cavity. After the external head, skull, airway and oral cavity are attached and the polyester has cured, the resulting physical model is placed in a heating device 640 to melt the wax, which leaves the airway and oral cavity open.

The physical model of the child's head allows the description and depiction of incidents that affect the airway. For example, the physical model can be used to assess the potential for a consumer product to inflict choking and aspiration injuries using physical models of the product in conjunction with the physical model. Although clear polyester is usually used to form the head due to its excellent optical properties, other materials more closely simulating the mechanical properties of the anatomy can also be used. Materials with different levels of hardness, such as silicon, can be molded to simulate more accurately the feel and action of the oral cavity and airway, as well as the surface features including the external auditory canal and eye socket.

A system and method consistent with the present invention allows for the construction of detailed computer models of specific anatomic areas, and computer-aided design programs allow these models to be manipulated to examine the effects of an almost limitless variety of possible injuries or alternations to anatomy. In addition, the use of the physical model can demonstrate more clearly some risks that are difficult to communicate with the virtual three-dimensional computer representation. The computer and physical models of body orifices and potential foreign bodies can be manipulated to assess risks of foreign body impaction or ingestion in a given body cavity in a patient of a specific age. Should the assessment point to a particular design feature as a source of increased risk, the manufacturer can redesign the product to decrease the risk before the product is produced and distributed.

It will be apparent to those skilled in the art that various modifications and variations can be made to disclosed embodiments of the present invention without departing from the scope or spirit of the invention. Other embodiments of the invention will be apparent to those skilled in the art from consideration of the specification and practice of the embodiments of the invention disclosed herein. The specification and examples should be considered exemplary, with the true scope and spirit of the invention being indicated by the following claims and their full range of equivalents.

What is claimed is:

1. A method for forming a physical model of a head for assessing injury risks, comprising the steps of:

obtaining digital images of an external head, skull, and at least one cavity of a human head;

generating stereo lithographic solids for the digital images of the external head, skull, and at least one cavity;

creating molds of the external head, skull, and at least one cavity using the corresponding stereo lithographic solids;

attaching together the molds of the external head, skull and at least one cavity;

pouring a hardener into the mold of the external head;

removing the moldable material in the mold of the at least one cavity to create an opening in the at least one cavity after the hardener has cured, and manipulating a physical model of a product in the at least one cavity to assess the risk of injury that the product may cause in the at least one cavity.

2. The method according to claim 1, wherein the step of obtaining digital images includes the substep of generating serial computed tomography (CT) scans of the external head, skull, and at least one cavity to form the digital images.

3. The method according to claim 1, wherein the step of obtaining a digital image of at least one cavity includes the substep of obtaining a digital image of an airway in the head.

4. The method according to claim 1, wherein the step of obtaining a digital image of at least one cavity includes the substep of obtaining digital images of an airway and an oral cavity in the head.

5. The method according to claim 4, wherein the step of obtaining a digital image of the airway includes the substep of generating a serial computed tomography (CT) scan of the airway.

6. The method according to claim 4, wherein the step of obtaining a digital image of the oral cavity includes the substeps of:

forming a cast of the oral cavity;

cutting the cast into a plurality of slices; and generating a digital image of the oral cavity from the slices of the cast.

7. The method according to claim 6, wherein the step of obtaining digital images of the airway and oral cavity includes the substep of manipulating the digital image of the oral cavity to coincide with the digital image of the airway to form a digital image of a single continuous cavity.

8. A physical modeling system for forming a physical model of a head, which is used in conjunction with a physical model of a product to assess injury risks, comprising:

an imaging device for generating digital images of an external head, a skull and at least one cavity of a human head;

a stereo lithograph, coupled to the imaging device, for generating stereo lithographic solids from the digital images of the external head, skull and at least one cavity;

a first processing device, coupled to the stereo lithograph, for creating molds of the external head, skull and at least one cavity using the corresponding stereo lithographic solids;

a second processing device, coupled to the first processing device, for casting moldable material into the mold of the at least one cavity; and a heating device, coupled to the second processing device, for melting the moldable material in the mold of the at least one cavity after the mold of the at least one cavity has been attached to the molds of the skull and the external head to thereby leave open the at least one cavity.

9. The physical modeling system of claim 8, further comprising:

means for pouring a hardener into the attached together molds of the external head, skull and at least one cavity and for curing the hardener before the heating device melts the moldable material cast in the mold of the at least one cavity.

10. The physical modeling system of claim 8, wherein the imaging device includes a serial computed tomography (CT) scan for generating CT scans that correspond to the digital images of the external head, skull and at least one cavity.

11. The physical modeling system of claim 8, wherein the digital image of the at least one cavity includes a digital image of an airway in the head.

12. The physical modeling system of claim 8, wherein the digital image of the at least one cavity includes digital images of an airway and an oral cavity in the head.

13. The physical modeling system of claim 12, further comprising:

a casting device, coupled to the stereo lithograph, for forming a casting of an oral cavity of a head.

14. The physical modeling system of claim 13, wherein the casting device further includes means for cutting the cast of the oral into a plurality of slices and for generating the digital image of the oral cavity from the slices of the cast.

15. The physical modeling system of claim 14, further comprising:

a processor, coupled to the imaging device, the casting device and the stereo lithograph, for manipulating the digital image of the oral cavity to coincide with the digital image of the airway to form a digital image of a single continuous cavity.

16. A method for forming a computer model of a head for assessing injury risks, the head including a plurality of cavities, comprising the steps of:

obtaining a digital image of a human head, the digital image of the head including a plurality of slices, each slice being a digital image of a layer of the digital image of the head;

creating a cast of the oral cavity of the head;

cutting the cast of the oral cavity into a plurality of slices;

obtaining a digital image of each slice of the cast of the oral cavity;

filling the cavities for the digital image of each slice from the digital image and each slice from the cast of the oral cavity with a color that contrasts with a color used for areas of each digital image other than the cavities;

forming the computer model of the head by placing the digital images of each slice from the digital image of the head and each slice from the cast of the oral cavity in their correct anatomical relationship;

forming a computer model of a product; and manipulating the computer model of the product with the computer model of the head to assess the risk of injury posed to the cavities of the head by the product.

17. The method according to claim 16, further comprising the step of:

converting the format of the computer model of the head to a digital exchange format to enable a computer aided design (CAD) program to manipulate the computer model of the head.

18. The method according to claim 16, wherein the step of obtaining a digital image of the head includes the substep of generating a serial computed tomography (CT) scan of the head.

19. The method according to claim 16, wherein the step of obtaining a digital image of the head includes the substep of generating a magnetic resonance image of the head.

20. The method according to claim 16, further comprising the step of:

reconstructing each of the cavities of the head to reduce the amount of data representing each cavity, each cavity being represented as a meshwork of intersecting lines.

21. The method according to claim 20, wherein the reconstructing step includes the substeps of filling a space between the digital images of each slice of a cavity with a plurality of estimated slices;

morphing the estimated slices to coincide with the digital images of each of the slices of the cavity to form a reconstructed cavity;

digitally filtering the reconstructed cavity;

converting a surface of the digitally filtered cavity to polygons; and applying an algorithm for reducing the amount of data representing the cavity.

22. A computer modeling system for forming a computer model of a head, which is used in conjunction with a computer model of a product to assess injury risks, comprising:

an imaging device for generating a digital image of a human head, the digital image of the head being divided into a plurality of slices, each slice being a digital image of a layer of the digital image of the head;

a casting device for creating a cast of the oral cavity of the human head, cutting the cast of the oral cavity into a plurality of slices and generating a digital image of each slice of the cast of the oral cavity;

a computer system, coupled to the imaging device and the casting device, having a processor and a memory for forming the computer model of the head from the digital images generated by the imaging device and the casting device, the processor executing modules stored in the memory, the memory being a computer readable medium and including:

a color contrast module for filling the cavities for the digital image of each slice from the digital image of the head and each slice from the cast of the oral cavity with a color that contrasts with a color used for areas of each digital image other than the cavities;

a formation module for forming the computer model of the head by placing the digital images of each slice from the digital image of the head and each slice from the cast of the oral cavity in their correct anatomical relationship;

a product module for forming a computer model of a product; and an analysis module for manipulating the computer model of the product with the computer model of the head to assess the risk of injury posed to the cavities of the head by the product.

* * * * *